United States Patent
Sawhney et al.

[11] Patent Number: 5,947,278
[45] Date of Patent: Sep. 7, 1999

[54] SINGLE-DOSE DOUBLE-CUP PACKAGE AND METHOD

[75] Inventors: Ravi K. Sawhney, Calabasas; Lance Hussey, Sherman Oaks, both of Calif.

[73] Assignee: Discus Dental Impressions, Inc., Culver City, Calif.

[21] Appl. No.: 08/972,400

[22] Filed: Nov. 18, 1997

[51] Int. Cl.⁶ ........................................ B65D 6/00
[52] U.S. Cl. .................. 206/216; 206/63.5; 220/797; 53/471
[58] Field of Search ..................... 206/216, 219, 206/63.5, 530, 534.1, 5.1, 461–471; 220/23.4, 783, 797, 793, 805; 53/471, 453, 485, 489

[56] References Cited

U.S. PATENT DOCUMENTS

| | | |
|---|---|---|
| 2,970,379 | 2/1961 | Hardgrove . |
| 3,327,391 | 6/1967 | Malm . |
| 3,460,552 | 8/1969 | Sturgeon .................................. 206/5.1 |
| 4,176,154 | 11/1979 | Miki et al. . |
| 4,577,757 | 3/1986 | Hustad et al. ........................... 206/461 |
| 4,717,057 | 1/1988 | Porteous . |
| 4,790,429 | 12/1988 | Fukushima .............................. 206/219 |
| 4,844,308 | 7/1989 | Porteous . |
| 5,009,056 | 4/1991 | Porteous . |
| 5,097,953 | 3/1992 | Gingras .................................. 206/467 |
| 5,375,698 | 12/1994 | Ewart et al. .............................. 206/5.1 |
| 5,396,986 | 3/1995 | Fountain et al. ........................ 206/63.5 |
| 5,509,530 | 4/1996 | Wilson ................................... 206/63.5 |
| 5,783,273 | 7/1998 | Yamamoto et al. ....................... 53/453 |

Primary Examiner—Paul T. Sewell
Assistant Examiner—Luan K. Bui
Attorney, Agent, or Firm—Christie, Paker & Hale, LLP

[57] ABSTRACT

A thermoformed dual-compartment flexible package and method for storing and dispensing the components of a polymerizable system such as the base and catalyst portions of an addition cured dental impression material. Mutually reactive constituents are isolated during storage. A first embodiment of the package includes two thermoplastic cups each having an open mouth circumscribed by an annular groove, separated by a slotted aperture. The package further includes a thermoformed flexible closure having a central projection between two annular projections. Two seals are formed by engaging the annular projections within the grooves. A second embodiment includes two thermoplastic cups separated by a slotted aperture, with each cup having an open mouth from whose rim depends an outwardly canted wall terminating at a recessed lip. The package further includes a thermoformed flexible closure having a central projection between two annular, concavely arcuate projections each having an outwardly flared rim terminating in a beveled edge. Two seals are formed by pressing each arcuate projection into a cup rim so that its flared rim contacts the canted wall and the edge contacts the lip.

23 Claims, 7 Drawing Sheets

SINGLE-DOSE DOUBLE-CUP PACKAGE AND METHOD

BACKGROUND OF THE INVENTION

1. Field of the Invention

The present invention relates to dental dispensing cups and, more particularly, to cups for simultaneously dispensing the base and catalyst pastes of addition cured vinyl silicones used in making dental impressions.

2. Description of the Related Art

Addition cured vinyl silicone materials such as polyvinylsiloxane elastomers are widely used in dentistry because they can provide highly accurate impressions, are simple to prepare and apply, and are available in a range of viscosities to accommodate different impression techniques. Typically, two paste admixtures having a putty-like consistency, a base portion and a catalyst portion, are constituted so that prior to their being combined one component needed for polymerization is missing in each portion. U.S. Pat. No. 4,806,575 (Waller et al., 1989) discloses suitable compositional ranges for components of base and catalyst portions combined in a 1-to-1 ratio. The base paste composition consists of, by weight: a vinyl-substituted long chain silicone, vinyl polydimethylsiloxane (10–60%); a hydrogen-substituted polysiloxane, hydropolydimethyl siloxane (1–10%), which acts as a cross-linking actuator only in the presence of a catalyst; a silica filler (20–80%); and liquid petroleum (0–15%). The catalyst paste composition consists of, by weight: vinyl polydimethylsiloxane (10–60%); cyclic vinyl siloxane (0–1%); chloroplatinic acid catalyst complex (0.1–5.0%); plasticizer (0–15%); filler (20–80%); and extremely finely divided platinum black (0.1–10,000 ppm). When the two pastes are combined, the platinum in the chloroplatinic acid activates the hydropolydimethyl siloxane which actuates cross-linking polymerization of the vinyl polydimethylsiloxane. Noticeable cross-linking (end of "working time") proceeds over a short time to almost total cross-linking ("setting time") of the resultant elastomeric silicone gum.

Because making an impression requires loading a fairly precise amount of the elastomeric material onto a dental tray, it is convenient to have available premeasured amounts of the base and catalyst portions in a single two-compartment dispensing package. However, juxtaposing or otherwise disposing these two admixtures in close proximity risks leakage of the catalyst into the compartment containing the cross-linking actuator or leakage of the actuator into the compartment containing the catalyst, particularly when a package is stored rather than being used soon after arriving in the dental office. The present invention overcomes this problem.

Dental dispensing cups are known in the art. U.S. Pat. No. 4,844,308 (Porteous, 1989) and U.S. Pat. No. 4,717,057 (Porteous, 1988) disclose a disposable sealed cup having an open mouth defined by a rim, filled with a dispensable material such as dental paste. The cup includes a removable closure overlying the open mouth and a ring-like finger mount extending from the rim. U.S. Pat. No. 3,327,391 (Malm, 1967) discloses a disposable, clear acetate, dental material cup containing dental medicaments or pumices and provided with a cellophane cover that may be heat sealed to the outwardly projecting rim of the cup. The cup bottom is provided with a projection adapted to be slip-fitted or snap-connected to a supporting non-disposable finger ring. U.S. Pat. No. 2,970,379 (Hardgrove, 1961) discloses a sterilizable, vertically disposed and pivotally connected, two-compartment, finger supportable dental tray for holding plastic filling materials, dental cleaning compounds or medications. The upper compartment forms a closure for the lower compartment, and the lower compartment is provided with a lateral rim from which extends a finger-engageable ring-like member.

Methods for configuring thermoplastic sheet into single- and multi-compartment packages, dispensing cups and similar articles also are known. For example, thermoformed dual-compartment packages having a sealed, removable closure are commonly used for cupcakes and other pastries. Specific to the dental arts, U.S. Pat. No. 5,009,056 (Porteous, 1991) discloses a method for preparing a substantially fluid impervious, sealed, dental paste dispensing cup having an integrated finger mount. Thermoplastic sheet is converted into a plurality of cup configurations by subjecting the sheet to the operations of a multi-cavity thermoforming machine, commonly called a vacuum former, wherein the sheet is heated to a pliable, plastic state and forced by a vacuum or other technique against the contours of each cavity. Upon cooling, the plastic retains the shape and details of the cavity. Various aspects of thermoforming, including sheet materials, machines, molds, thermoforming techniques, thermoforming variables and finishing are extensively considered in the following reference: W. K. McConnell Jr., Thermoforming, *Modern Plastic Encyclopedia*, Vol. 45, No. 14a, pp. 776–792, McGraw-Hill, 1968–1969.

One thermoforming method for producing cup-shaped "deep-draw"-formed articles from a plastic sheet is the plug-assist pressure method. First, a heated and softened sheet is forced into a female mold by a short-nosed plug. Then pressured air is introduced between the plug and sheet to allow the sheet to come into full contact with the mold. The sheet is then cooled to obtain the shaped article. This method makes possible adjustment of wall thickness, and overcomes a disadvantage of the conventional vacuum method in that the bottom thickness of the cup is extremely thinned. However, when a crystalline thermoplastic resin sheet such as polypropylene sheet is used, accurate adjustment of the plug configuration becomes critical. It then is necessary to determine the optimum plug configuration and finely tailor the plug shape for each thermoformed article. U.S. Pat. No. 4,176,154 (Miki et al., 1979) discloses a method for producing a cup-shaped article which uses a concave forming mold and a recessed ancillary mold in mutual opposition. The ancillary mold includes a vertically movable molding assist. By introducing a pressured fluid into the forming mold, a preheated thermoplastic sheet interposed between the forming and ancillary molds is expanded into the ancillary mold while the molding assist is moving and in contact with the sheet. When the molding assist reaches a predetermined position, a pressured fluid introduced into the ancillary mold presses the sheet against the interior surface of the forming mold, thereby forming the desired shape. The method is applicable to deep-draw forming of cups having a depth-to-opening diameter ratio greater than 0.2.

Heretofore, no package has been provided which meets the specific requirements of addition cured dental impression materials. What is needed is a dual-compartment, air-tight sealed package which can be conveniently thermoformed, which will not be susceptible to leakage between compartments even after a long storage period, and which allows convenient dispensing of the base and catalyst portions.

OBJECTS OF THE INVENTION

Accordingly, it is an object of the present invention to provide an air-tight sealed dual-compartment package adapted to contain the base and catalyst portions of an addition cured dental impression material, whose configuration prevents wicking or creeping of ingredients from one compartment to the other.

Another object of the invention is to provide a dual-compartment package which can be manufactured using a conventional thermoforming method.

A further object of the invention is to provide an air-tight sealed dual-compartment package that is simple to manufacture and readily mass-produced.

A still further object of the invention is to provide a dual-compartment package for conveniently dispensing approximately equal amounts of base and catalyst pastes.

Other objects of the invention will become evident when the following description is considered with the accompanying drawing figures. In the figures and description, numerals indicate the various features of the invention, like numerals referring to like features throughout both the drawings and the description.

SUMMARY OF THE INVENTION

These and other objects are achieved by the present invention which provides a dual-compartment package for storing and dispensing the components of a polymerizable system such as the base and catalyst portions of an addition cured dental impression material, while isolating mutually reactive constituents during storage.

In a first aspect the invention provides a flexible package for separably storing and simultaneously dispensing two materials. The package includes two receptacles each having an open end bounded circumferentially by a rim, with a material disposed within each receptacle. The receptacles are connected by a flexible bridge. A flexible closure is superposed on the receptacles and connecting bridge. In a first embodiment, the closure is sealingly engaged with and reversibly disengaged from each open end by means of an annular groove circumscribing the rim, determined by a pair of walls tapering to a concavely arcuate bottom portion, within which is received an annular projection depending from the closure, determined by a pair of walls tapering to a convexly arcuate bottom portion. Each wall tapers at a common angle so that the projection closely conforms to the groove. In a second embodiment, the closure is sealingly engaged with and reversibly disengaged from each open end by means of an annular recessed lip circumscribed by the rim and a circumferential wall, canted downwardly outward and connecting the rim and lip, which are brought into pressing contact with a projection depending from the closure. The projection has a rim, bounded by a beveled edge, which flares outwardly at the same angle as the canted wall. The beveled edge contacts the lip and the flared rim contacts the circumferential wall.

In a second aspect the invention provides a flexible package for storing and dispensing the components of a polymerizable system. The package includes a first receptacle having an open end and containing a polymerizable material and a polymerization actuator, and a second receptacle having an open end and containing the polymerizable material and a polymerization catalyst. A flexible bridge connecting the two receptacles has a transversely disposed slotted aperture. A flexible closure is superposed on the two receptacles and connecting bridge. The invention further provides means for sealingly engaging and reversibly disengaging the closure with and from the open ends.

In a third aspect the invention provides a package for containing and isolating the two portions of a binary admixture. The package includes two molded thermoplastic cups each having an open mouth determined by a circular, convexly arcuate rim having a proximal portion and a distal portion. Each rim is circumscribed by an annular molded groove disposed between the rim distal portion and a generally planar thermoplastic package peripheral portion. A flexible bridge connecting the two cups has a transversely disposed slotted aperture having an inwardly tapering central portion symmetrically disposed between two outwardly tapering outer portions. The aperture is proximate along its central portion to each rim proximal portion. The package further includes a thermoplastic flexible, generally planar closure having a transversely disposed, molded central projection adapted to be closely received within the aperture. The central projection is disposed between two annular molded projections each adapted to be closely received within one of the grooves, thereby forming an air-tight seal.

In a fourth aspect the invention provides a package for containing and isolating the two portions of a binary admixture. The package includes two molded thermoplastic cups each having an open mouth bounded by a circular rim. Each rim is disposed between a generally planar thermoplastic package peripheral portion and a flexible bridge connecting the two cups. The bridge has a transversely disposed slotted aperture. Depending from each rim is a generally circumferential wall, canted outwardly, which terminates at a circumferential recessed lip generally parallel to the bridge and package peripheral portions. A thermoplastic flexible, generally planar closure includes a transversely disposed, molded central projection adapted to be closely received within the aperture. The central projection is disposed between two annular, concavely arcuate projections. Each annular projection is circumscribed by a beveled edge determined by a rim flaring outwardly at the angle of the canted wall. Each annular projection is receivable within one of the open mouths so that the beveled edge contacts the lip and the flared rim contacts the circumferential wall, thereby forming an air-tight seal.

In a fifth aspect the invention provides a method for containing and storing in mutual isolation a base portion admixture and a catalyst portion admixture of a dispensable dental paste material. The method includes: (a) thermoforming in a first flexible thermoplastic sheet, a generally rectangular dual-compartment package including generally proximate first and second cups separated by a flexible bridge having a slotted aperture, with each cup circumscribed by an annular groove; (b) thermoforming in a second flexible thermoplastic sheet, a generally rectangular, generally planar closure including a central, transversely disposed projection adapted to be closely received within the aperture, and further including two annular, downwardly tapering projections each adapted to be closely received within one of the grooves; (c) putting a predetermined amount of the base portion admixture into one cup, and a predetermined amount of the catalyst portion admixture into the other cup; and (d) superposing the closure over the cups and bridge and applying a pressure so that the central projection is closely received within the aperture, and each annular projection is closely received within one of the grooves, thereby forming two air-tight seals.

In a sixth aspect the invention provides a method for containing and storing in mutual isolation a base portion admixture and a catalyst portion admixture of a dispensable dental paste material. The method includes: (a) thermoforming in a first flexible thermoplastic sheet, a generally rectangular dual-compartment package including generally proximate first and second cups separated by a flexible bridge having a slotted aperture, with each cup bounded by a circular rim from which depends a generally circumferential wall canted downwardly outward and terminating at a circumferential recessed lip; (b) thermoforming in a second flexible thermoplastic sheet, a generally rectangular, generally planar closure including a transversely disposed central projection adapted to be closely received within the aperture, the central projection disposed between two annular, concavely arcuate first and second projections, each projection having an outwardly flared rim terminating in a beveled edge; (c) putting a predetermined amount of the base portion admixture into one cup, and a predetermined amount of the catalyst portion admixture into the other cup; and (d) superposing the closure over the cups and bridge and applying a pressure so that the central projection is received within the aperture, and each annular projection is closely received within a cup rim so that the flared projection rim contacts the circumferential wall and the beveled edge contacts the lip, thereby forming two air-tight seals.

A more complete understanding of the present invention and other objects, aspects and advantages thereof will be gained from a consideration of the following description of the preferred embodiment read in conjunction with the accompanying drawings provided herein.

DESCRIPTION OF THE PREFERRED EMBODIMENTS

Figure 1:
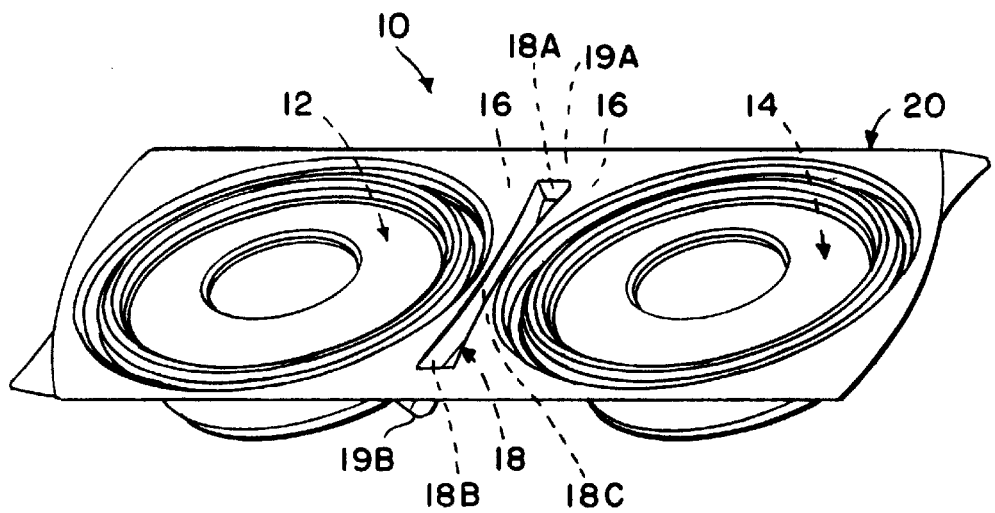
FIG. 1 is a perspective view of a first embodiment of a double-cup package according to the invention, including two thermoplastic molded cups separated by a slotted aperture bounded by opposed end-tabs, and sealed by a removable closure formed from a thermoplastic flexible sheet.
Figure 2:
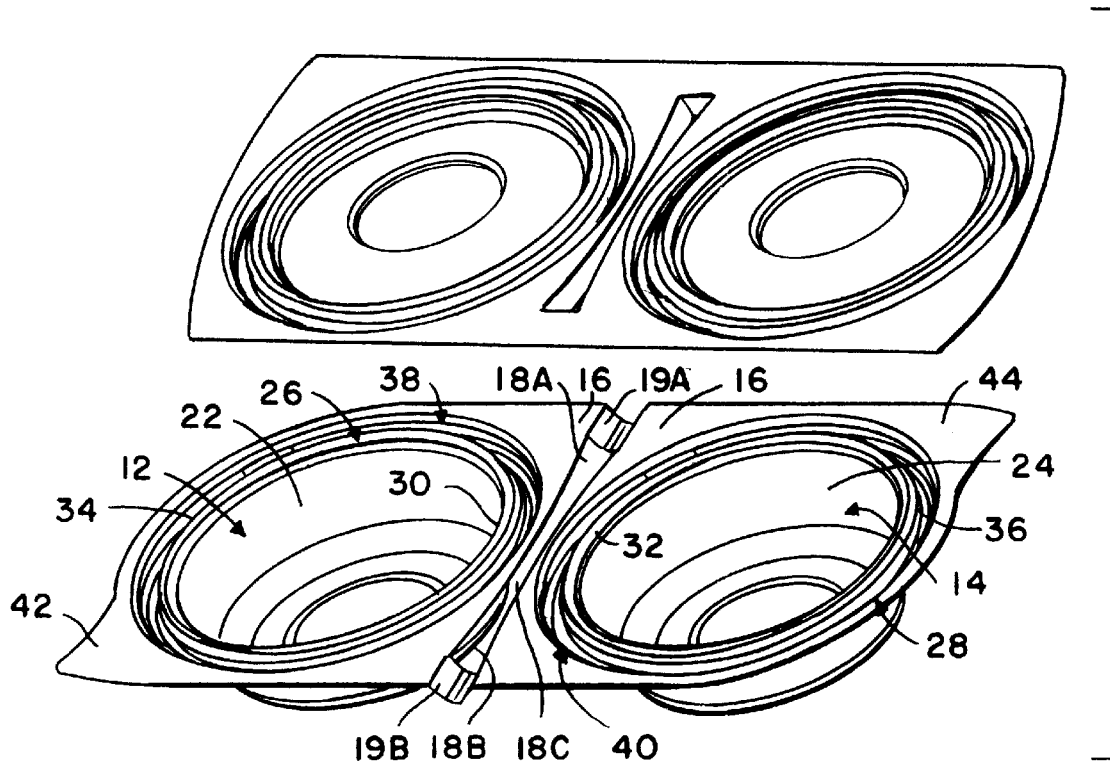
FIG. 2 is an exploded perspective view of the FIG. 1 package wherein the cups are bottom-down.

While the present invention is open to various modifications and alternative constructions, the preferred embodiments shown in the drawings will be described herein in detail. It is to be understood, however, there is no intention to limit the invention to the particular forms disclosed. On the contrary, it is intended that the invention cover all modifications, equivalences and alternative constructions falling within the spirit and scope of the invention as expressed in the appended claims.

The invention relates to an article of manufacture which is primarily intended for storing and dispensing two pastes which are portions of a binary admixture and which need to be segregated until the admixture is formed. However, the invention is not limited to particular types of material to be stored and dispensed, and can be used for storing and dispensing any two materials, particularly those which require mutual isolation.

Figure 4:
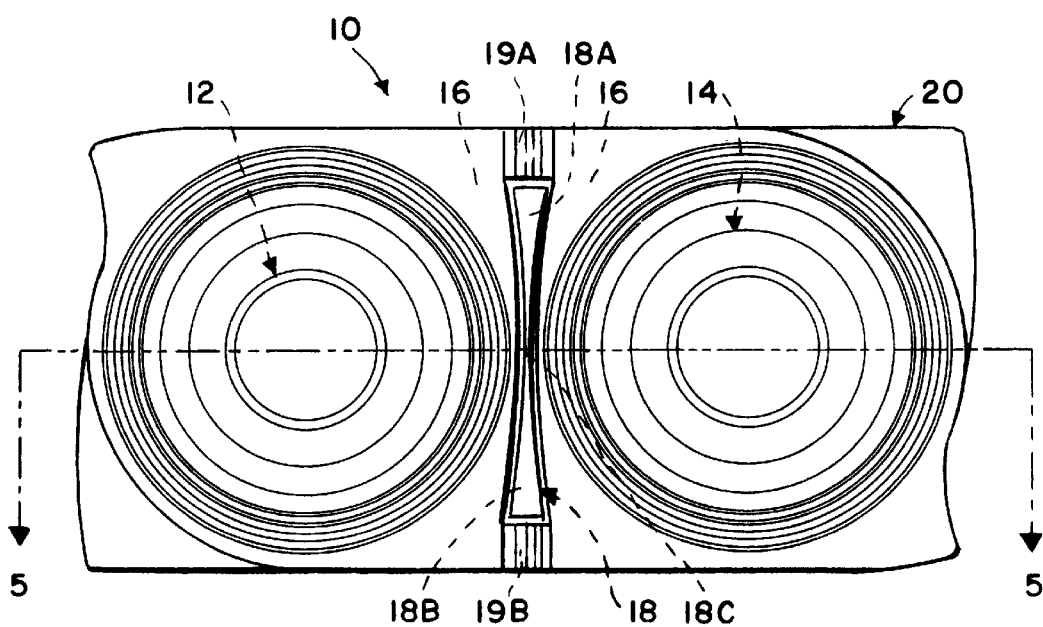
FIG. 4 is a top plan view of the FIG. 1 package.

Referring to FIGS. 1 and 4, a first embodiment of a flexible package 10 according to the invention includes first and second molded thermoplastic cups 12, 14 connected by a generally planar flexible bridge 16 having a generally transversely disposed slotted aperture 18 having an inwardly tapering central portion 18C symmetrically disposed between first and second outwardly tapering outer portions 18A, 18B, and bounded by opposed trough-shaped end-tabs 19A, 19B which facilitate flexure of the bridge 16 when the package contents are dispensed. Package 10 further includes a thermoplastic flexible, generally planar closure 20. Preferably, the package is fabricated from polypropylene sheet using a conventional thermoforming process.

Figure 5:
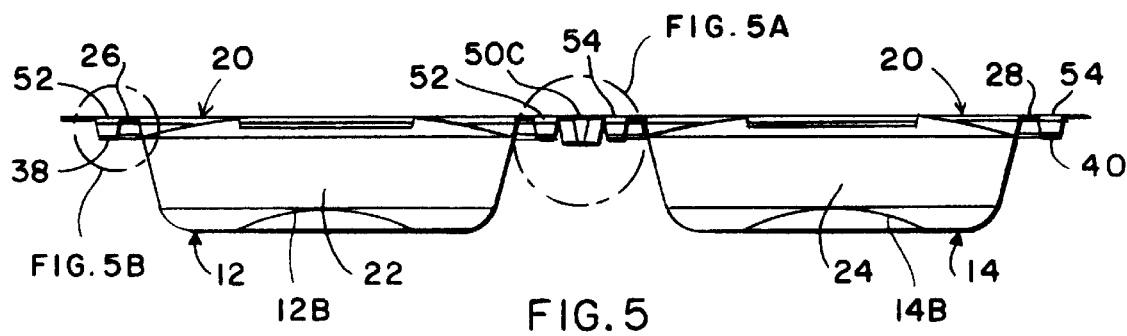
FIG. 5 is a sectional view of the FIG. 4 package along the cutting plane 5—5.
Figure 5A:
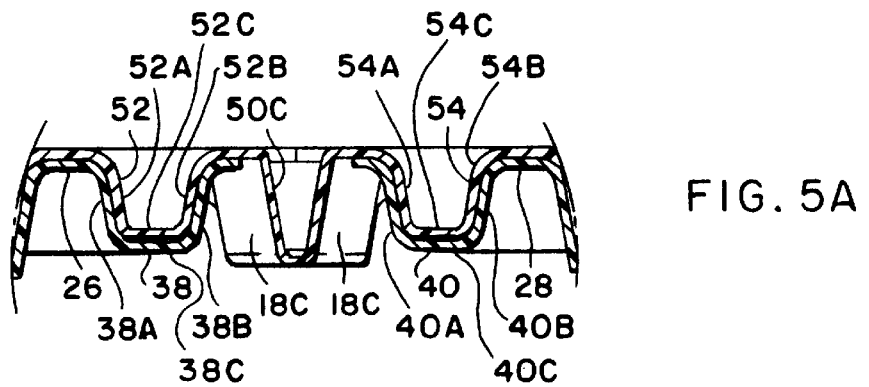
FIG. 5A is a detail sectional view of the "FIG. 5A" portion of FIG. 5.
Figure 5B:
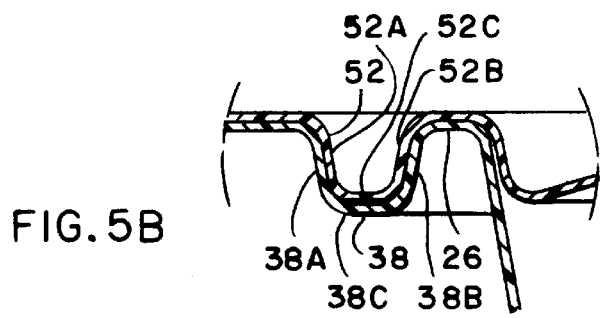
FIG. 5B is a detail sectional view of the "FIG. 5B" portion of FIG. 5.

Referring to FIGS. 2, 5, 5A and 5B, the conically symmetric, downwardly tapering cups 12, 14 each have an open mouth 22, 24, respectively, determined by a generally circular, convexly arcuate rim 26, 28, respectively, having a proximal portion 30, 32, respectively, and a distal portion 34, 36, respectively. Rims 26, 28 each are circumscribed by a generally annular, downwardly tapering molded groove 38, 40, respectively, disposed distally between the rim distal portion 34, 36, respectively, and a generally planar package peripheral portion 42, 44, respectively, and disposed proximally between the rim proximal portion 30, 32, respectively, and bridge 16. Referring to FIGS. 5A and 5B, grooves 38, 40 are determined, respectively, by outer and inner walls 38A, 38B and 40A, 40B which each taper downwardly at an angle of about 5 degrees to a concave arcuately-shaped bottom portion 38C, 40C, respectively. Preferably, cup 12, rim 26 and groove 38 have the same configuration and dimensions, respectively, as cup 14, rim 28 and groove 40.

Referring to FIGS. 3, 5, 5A and 5B, the closure 20 includes a central, transversely disposed molded projection 50. Projection 50 includes an inwardly tapering central portion 50C symmetrically disposed between first and second outwardly tapering outer portions 50A, 50B. Thus, the projection 50 tapers inwardly in conformance with the configuration of aperture 18 so as to be closely receivable within the aperture. Closure 20 further includes first and second generally annular, molded projections 52, 54. Referring to FIGS. 5A and 5B, projections 52, 54 are determined, respectively, by outer and inner walls 52A, 52B and 54A, 54B which each taper downwardly at an angle of about 5 degrees to a convex arcuately-shaped bottom portion 52C, 54C, respectively. Thus, projections 52, 54 closely conform to annular grooves 38, 40, respectively, so as to be sealingly receivable within the grooves. Preferably, projections 52 and 54 have the same configuration and dimensions.

Figure 3:
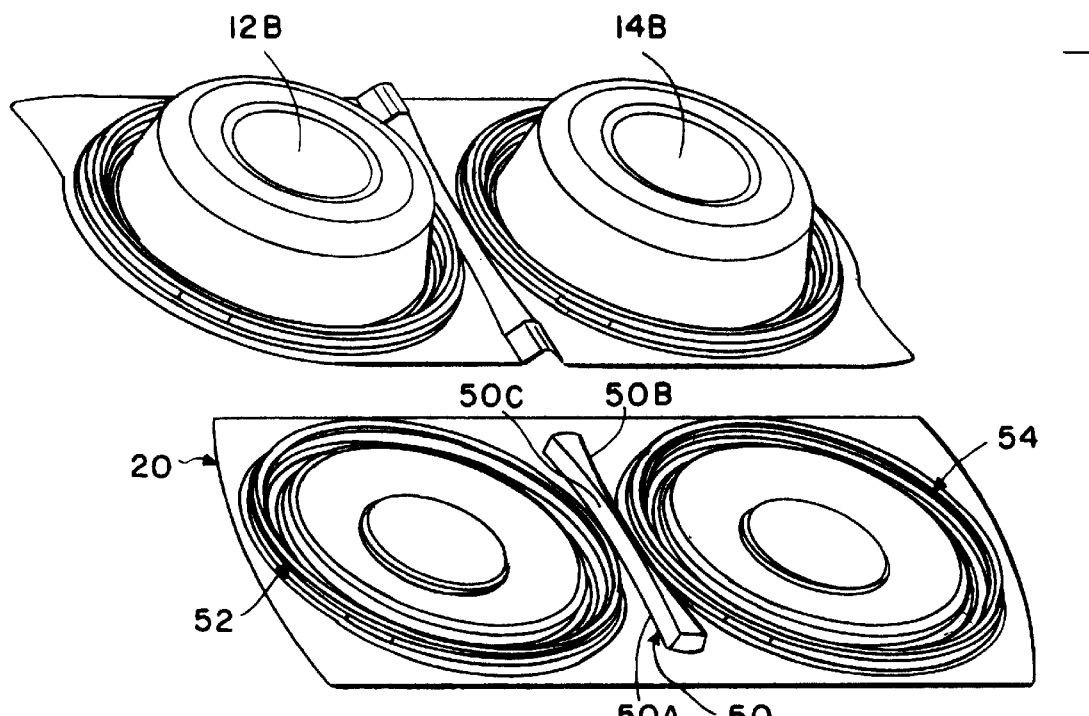
FIG. 3 is an exploded perspective view of the FIG. 1 package wherein the cups are bottom-up.
Figure 6:
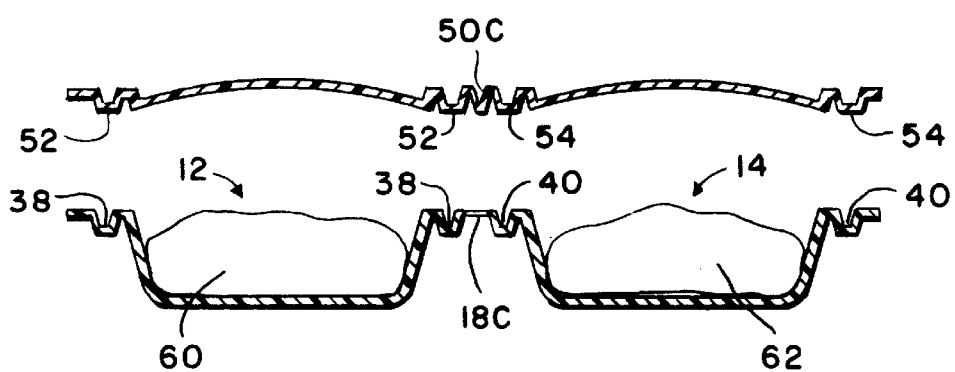
FIG. 6 is a schematic exploded cross-sectional view of the FIGS. 1, 5 package wherein each cup contains a dispensable material.

FIG. 6 depicts schematically that approximately equal amounts of two materials 60, 62 are inserted, respectively, into cups 12, 14 prior to sealingly engaging projections 52, 54 within annular grooves 38, 40, respectively. In an illustrative embodiment, the materials are a base portion and a catalyst portion of a dispensable dental paste. Typically, the dental paste is an addition cured elastomeric silicone used for making dental impressions whose base portion includes a vinyl polydimethylsiloxane and a hydropolydimethyl siloxane, and whose catalyst portion includes a vinyl polydimethylsiloxane, a cyclic vinyl siloxane, a chloroplatinic acid complex, and platinum black. Referring to FIGS. 3 and 5, the cup bottoms 12B, 14B, which as a result of the thermoforming process generally are thinner than the cup walls, can be easily depressed to facilitate dispensing of the materials. The cup bottoms are shown depressed in FIG. 5.

Figure 7:
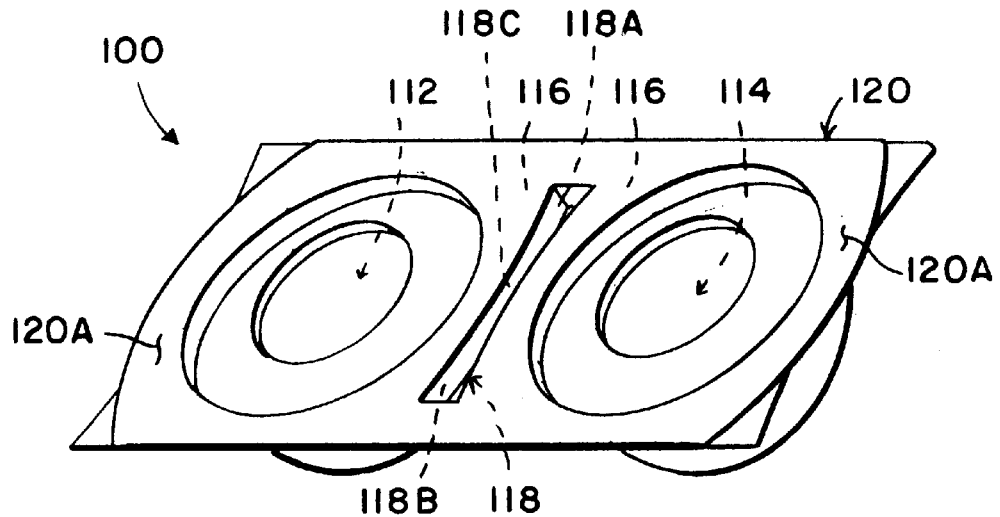
FIG. 7 is a perspective view of a second embodiment of a double-cup package according to the invention, including two thermoplastic molded cups separated by a slotted aperture and sealed by a removable closure formed from a thermoplastic flexible sheet.
Figure 8:
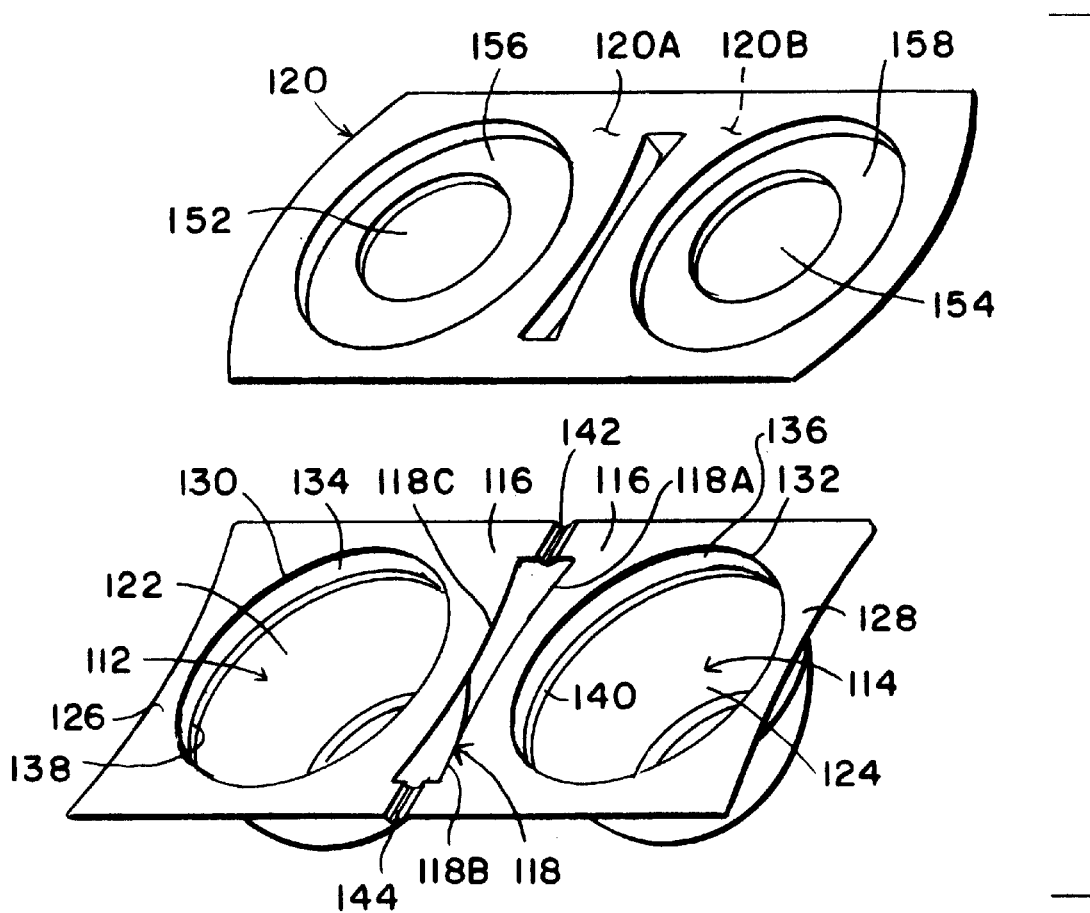
FIG. 8 is an exploded perspective view of the FIG. 7 package wherein the cups are bottom-down.
Figure 10:
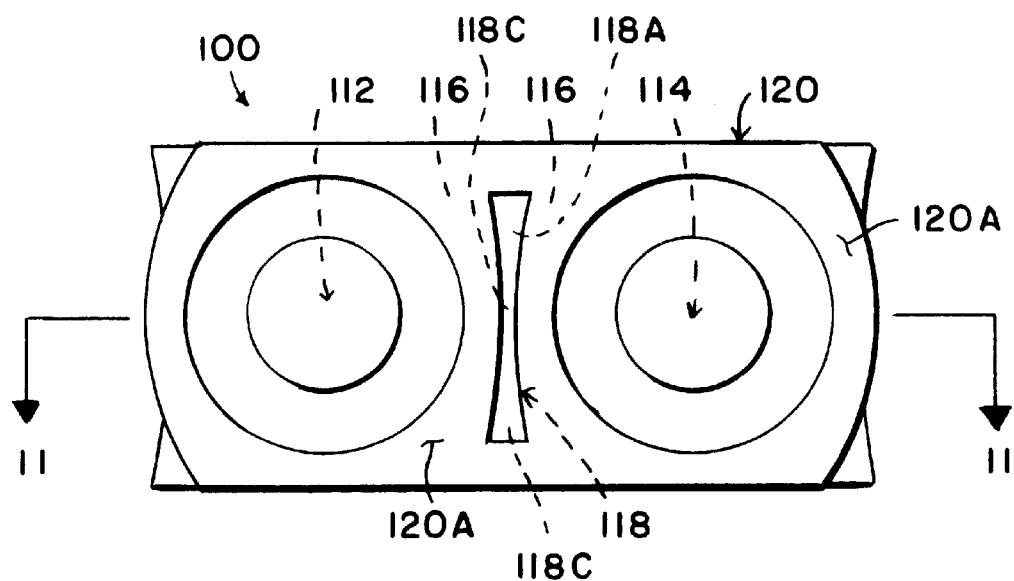
FIG. 10 is a top plan view of the FIG. 7 package.

Referring to FIGS. 7, 8 and 10, a second embodiment of a flexible package 100 according to the invention includes first and second thermoplastic cups 112, 114 connected by a generally planar flexible bridge 116 having a generally transversely disposed slotted aperture 118 having an inwardly tapering central portion 118C symmetrically disposed between first and second outwardly tapering outer portions 118A, 118B. Package 100 further includes a thermoplastic flexible closure 120 determined by upper and lower surfaces 120A, 120B. Preferably, the package is fabricated from polypropylene sheet using a conventional thermoforming process.

Referring to FIG. 8, the conically symmetric, downwardly tapering cups 112, 114 each have an open mouth 122, 124, respectively, disposed between the bridge 116 and a generally planar package peripheral portion 126, 128, respectively. The mouths 122, 124 are determined by a generally circular rim 130, 132, respectively, bounding an almost vertical circumferential wall 134, 136, respectively, canted downwardly outward at an angle of about 5 degrees. Walls 134, 136 terminate, respectively, at a circumferential recessed lip 138, 140 generally parallel to bridge 116 and package portions 126, 128. Still referring to FIG. 8, the aperture 118 is disposed between molded depressions 142, 144 which facilitate flexure of the bridge 116 when the package contents are dispensed. Preferably, cup 112, rim 130, wall 134 and lip 138 have the same configuration and dimensions, respectively, as cup 114, rim 132, wall 136 and lip 140.

Figure 9:
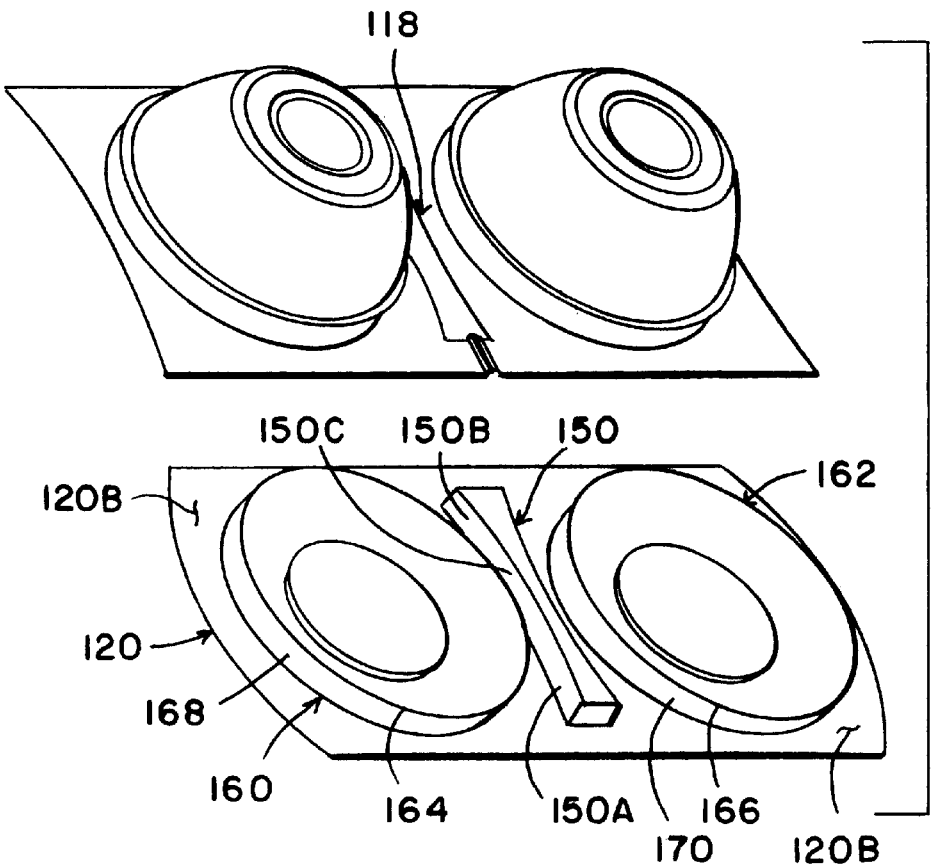
FIG. 9 is an exploded perspective view of the FIG. 7 package wherein the cups are bottom-up.

Referring to FIG. 9, the closure 120 includes a central, transversely disposed molded projection 150 having an inwardly tapering central portion 150C symmetrically disposed between first and second outwardly tapering outer portions 150A, 150B. Thus, projection 150 conforms to the contours of aperture 118 so as to be closely receivable within the aperture.

Figure 11:
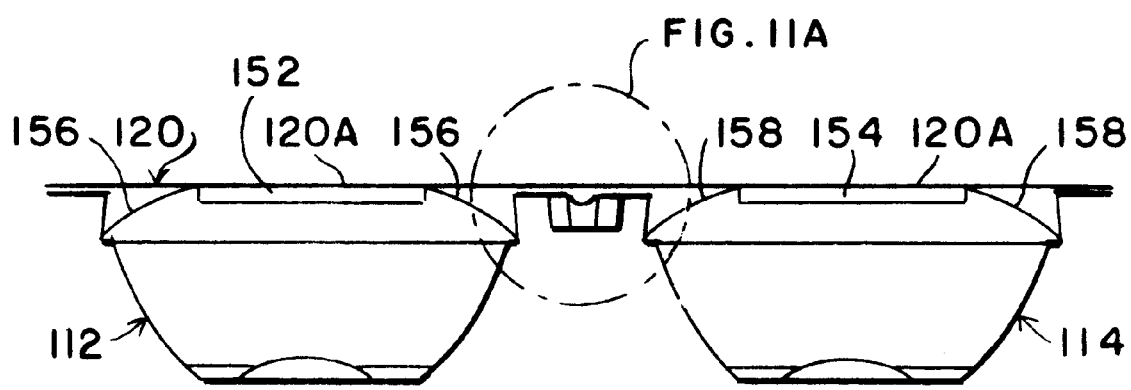
FIG. 11 is a sectional view of the FIG. 10 package along the cutting plane 11—11.
Figure 11A:
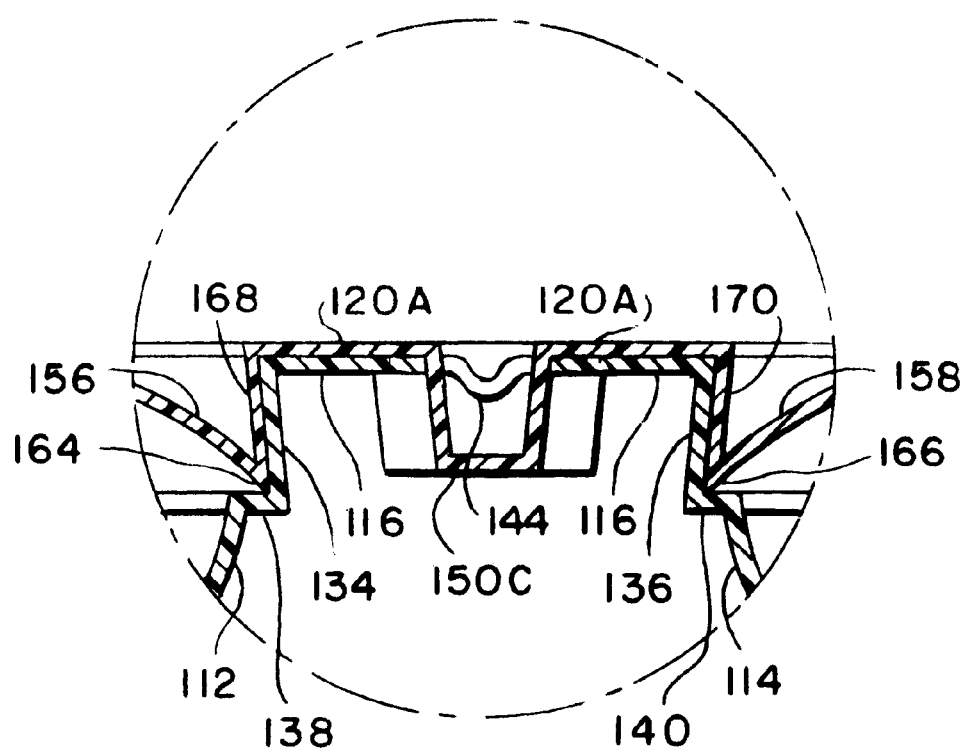
FIG. 11A is a detail sectional view of the "FIG. 11A" portion of FIG. 11.

Referring to FIGS. 8 and 11, molded into upper surface 120A are first and second generally circular molded depressions 152, 154 each circumscribed, respectively, by a convexly arcuate molded annular region 156, 158 which slopes outwardly and downwardly. Referring to FIGS. 9, 11 and 11A, molded into lower surface 120B are first and second concavely arcuate annular projections 160, 162 each circumscribed, respectively, by a beveled edge 164, 166 determined, respectively, by a rim 168, 170 which flares outwardly at an angle of about 5 degrees. Projections 160, 162 are the counterparts, respectively, to annular regions 156, 158. That is, the thermoforming operation that molds the annular regions also molds the projections. As shown in FIG. 11A, sealing of cups 112, 114 is effected when annular regions 160, 162 are fitted into mouths 122, 124, respectively, so that rims 168, 170 come into pressing contact, respectively, with walls 134, 136 and edges 164, 166 come into pressing contact, respectively, with lips 138, 140.

Figure 12A:
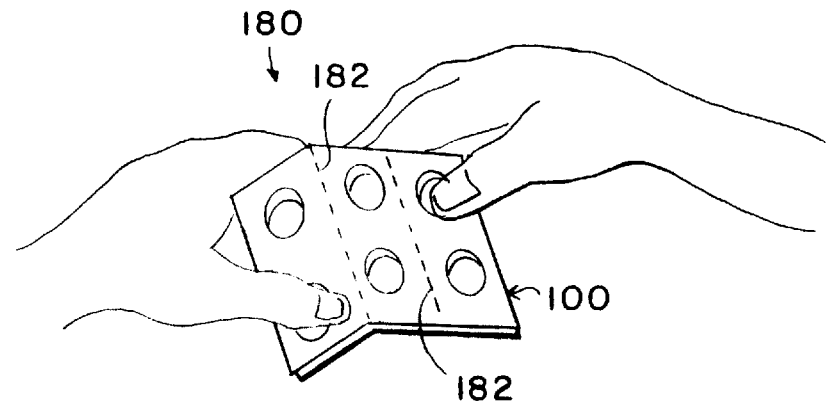
FIG. 12A illustrates separating a FIG. 7 package from a three-package strip.
Figure 12B:
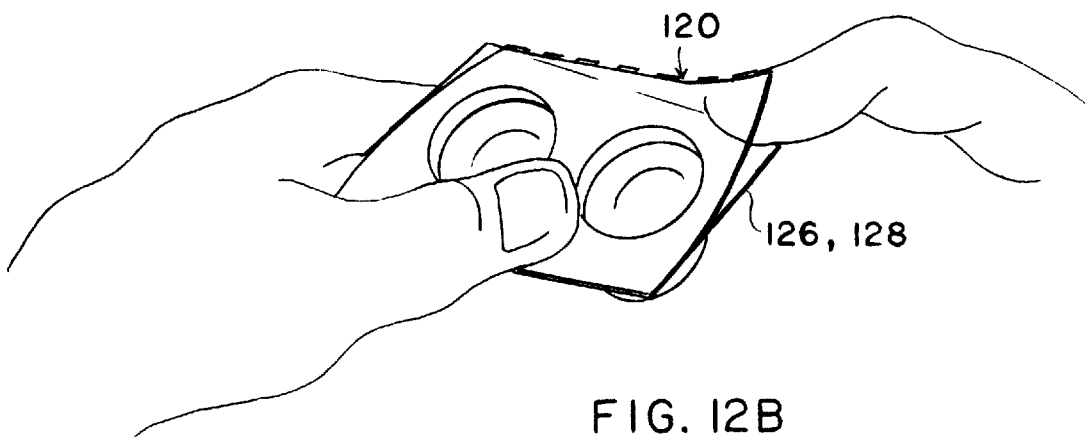
FIG. 12B illustrates removing the closure from the FIG. 12A package.
Figure 12C:
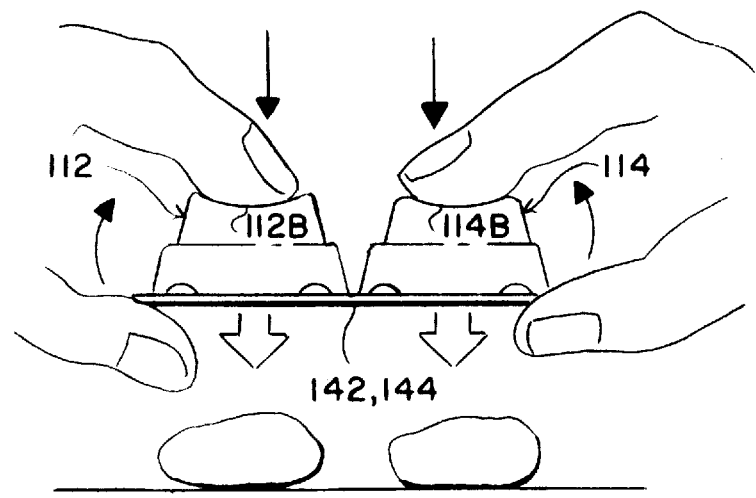
FIG. 12C illustrates dispensing simultaneously the contents of both cups of the FIG. 7 package.

FIG. 12A shows an three-package strip 180 of packages 100, wherein contiguous packages are connected along a lateral perforated boundary 182, so that an end package is easily separable from the strip. Alternatively, each package 100 may be discrete. FIG. 12B shows a user starting to peel away closure 120 from a package peripheral portion, 126 or 128. Continuing the peeling process causes projections 160, 162 to disengage from contact with walls 134, 136 and lips 138, 140, respectively (see FIG. 11A), thereby opening cups 112, 114 to expose material portions 60, 62. FIG. 12C shows the user dispensing the material portions from the cups by pressing a forefinger against each cup bottom 112B, 114B while flexing upwardly the package along the depressions 142, 144.

What is claimed is:

1. A flexible package for separably storing and simultaneously dispensing a first material and a second material, comprising:

a first receptacle having a first open end bounded circumferentially by a first rim, the first material disposed within the receptacle;

a second receptacle having a second open end bounded circumferentially by a second rim, the second material disposed within the receptacle, the first and second receptacles connected by a flexible bridge;

a flexible closure superposed on the first and second receptacles and connecting bridge; and means for sealingly engaging and reversibly disengaging the closure with and from the first and second open ends.

2. The package of claim 1, wherein said means for sealingly engaging and reversibly disengaging the closure with and from the first and second open ends comprises:

generally annular first and second grooves circumscribing, respectively, said first and second rims, each groove determined by an outer wall and an inner wall, each wall tapering downwardly at a predetermined angle to a concavely arcuate bottom portion; and generally annular first and second projections depending from the closure, each projection determined by an outer wall and an inner wall, each wall tapering downwardly at said predetermined angle to a convexly arcuate bottom portion, each projection receivable within and conforming to one of said grooves.

3. The package of claim 2, wherein said angle is about 5 degrees.

4. The package of claim 1, wherein said means for sealingly engaging and reversibly disengaging the closure with and from the first and second open ends comprises:

generally annular first and second recessed lips circumscribed, respectively, by said first and second rims, a circumferential wall connecting each rim and lip, each wall canted downwardly outward at a predetermined angle; and generally annular, concavely arcuate first and second projections depending from the closure, each projection circumscribed by a beveled edge determined by a rim flaring outwardly at said predetermined angle, each projection receivable within one of said open ends so that said beveled edge contacts said lip and said flared rim contacts said circumferential wall.

5. The package of claim 4, wherein said angle is about 5 degrees.

6. A flexible package for storing and dispensing the components of a polymerizable system, said package comprising:
 a first receptacle having an open end, a polymerizable material and a polymerization actuator disposed within said receptacle;
 a second receptacle having an open end, corresponding polymerizable material and a polymerization catalyst disposed within said receptacle;
 a flexible bridge connecting the first and second receptacles, said bridge having a generally transversely disposed slotted aperture;
 a flexible closure superposed on the first and second receptacles and connecting bridge; and
 means for sealingly engaging and reversibly disengaging the closure with and from the first and second open ends.

7. The package of claim 6, wherein said means for sealingly engaging and reversibly disengaging the closure with and from the first and second open ends comprises first and second grooves circumscribing, respectively, said open ends, each groove determined by an outer wall and an inner wall, each wall tapering downwardly at a predetermined angle to a concavely arcuate bottom portion, and further comprises first and second projections depending from the closure, each projection determined by an outer wall and an inner wall, each wall tapering downwardly at said predetermined angle to a convexly arcuate bottom portion.

8. A package for containing and isolating the two portions of a binary admixture, comprising:
 first and second molded thermoplastic cups each having an open mouth determined by a generally circular, convexly arcuate rim having a proximal portion and a distal portion, each rim circumscribed by a generally annular molded groove disposed between the rim distal portion and a generally planar thermoplastic package peripheral portion;
 a flexible bridge connecting the first and second cups, said bridge having a generally transversely disposed slotted aperture, said aperture having an inwardly tapering central portion symmetrically disposed between first and second outwardly tapering outer portions, said aperture proximate along said central portion to each rim proximal portion; and
 a thermoplastic flexible, generally planar closure having a transversely disposed, molded central projection adapted to be closely received within said aperture, said central projection disposed between first and second generally annular molded projections each adapted to be closely received within one of said grooves, thereby forming an air-tight seal.

9. The package of claim 8, wherein:
 the cups are conically symmetric and taper downwardly, and the cup mouths have a common diameter;
 the transversely disposed central projection tapers symmetrically inwardly in conformance with said aperture;
 the annular grooves taper downwardly; and
 the first and second annular molded projections taper downwardly in conformance with the grooves.

10. The package of claim 9, wherein the cups, rims, grooves, and annular molded projections have, respectively, the same configuration and dimensions.

11. The package of claim 10, wherein each cup is filled with a dispensable dental paste material.

12. The package of claim 11, wherein one cup contains a base portion and the other cup contains a catalyst portion of an addition cured elastomeric silicone material.

13. A package for containing and isolating the two portions of a binary admixture, comprising:
 first and second molded thermoplastic cups each having an open mouth bounded by a generally circular rim, each rim disposed between a generally planar thermoplastic package peripheral portion and a flexible bridge connecting the first and second cups, said bridge having a generally transversely disposed slotted aperture, a generally circumferential wall depending from each rim, each wall canted downwardly outward at a predetermined angle, each wall terminating at a generally circumferential recessed lip generally parallel to said bridge and said package peripheral portions; and
 a thermoplastic flexible, generally planar closure having a transversely disposed, molded central projection adapted to be closely received within said aperture, said central projection disposed between first and second generally annular, concavely arcuate molded first and second projections, each projection circumscribed by a beveled edge determined by a rim flaring outwardly at said predetermined angle, each projection receivable within one of said open mouths so that said beveled edge contacts said lip and said flared projection rim contacts said circumferential wall, thereby forming an air-tight seal.

14. The package of claim 13, wherein the cups are conically symmetric and taper downwardly, and the cup mouths have a common diameter.

15. The package of claim 14, wherein the cups, cup rims, walls, lips, and annular projections have, respectively, the same configuration and dimensions.

16. The package of claim 15, wherein each cup is filled with a dispensable dental paste material.

17. The package of claim 16, wherein one cup contains a base portion and the other cup contains a catalyst portion of an addition cured elastomeric silicone material.

18. A method for containing and storing in mutual isolation a base portion admixture and a catalyst portion admixture of a dispensable dental paste material, comprising the steps of:
 thermoforming in a first flexible thermoplastic sheet, a generally rectangular dual-compartment package comprising generally proximate first and second cups separated by a flexible bridge having a slotted aperture, each cup circumscribed by a generally annular groove;
 thermoforming in a second flexible thermoplastic sheet, a generally rectangular, generally planar closure comprising a central, transversely disposed, downwardly tapering projection adapted to be closely received within said aperture, and first and second generally annular, downwardly tapering projections each adapted to be closely received within one of said grooves;
 putting a predetermined amount of the base portion admixture into one cup, and a predetermined amount of the catalyst portion admixture into the other cup; and
 superposing the closure over the cups and bridge and applying a pressure so that said central projection is closely received within said aperture, and each said annular projection is closely received within one of said grooves, thereby forming two air-tight seals.

19. The method of claim 18, wherein said amounts of base portion admixture and catalyst portion admixture are about equal.

20. The method of claim 19, wherein said first and second thermoplastic sheets are polypropylene.

21. A method for containing and storing in mutual isolation a base portion admixture and a catalyst portion admixture of a dispensable dental paste material, comprising the steps of:

thermoforming in a first flexible thermoplastic sheet, a generally rectangular dual-compartment package comprising generally proximate first and second cups separated by a flexible bridge having a slotted aperture, each cup bounded by a generally circular rim, each rim having depending therefrom a generally circumferential wall canted downwardly outward, each wall terminating at a circumferential recessed lip;

thermoforming in a second flexible thermoplastic sheet, a generally rectangular, generally planar closure comprising a transversely disposed central projection adapted to be closely received within said aperture, said central projection disposed between generally annular, concavely arcuate first and second projections, each projection having an outwardly flared rim terminating in a beveled edge;

putting a predetermined amount of the base portion admixture into one cup, and a predetermined amount of the catalyst portion admixture into the other cup; and superposing the closure over the cups and bridge and applying a pressure so that said central projection is received within said aperture, and each said annular projection is closely received within one of said cup rims so that said flared projection rim contacts said circumferential wall and said beveled edge contacts said lip, thereby forming two air-tight seals.

22. The method of claim 21, wherein said amounts of base portion admixture and catalyst portion admixture are about equal.

23. The method of claim 22, wherein said first and second thermoplastic sheets are polypropylene.

* * * * *